(12) United States Patent
Mori et al.

(10) Patent No.: US 7,837,617 B2
(45) Date of Patent: Nov. 23, 2010

(54) INTRABODY INTRODUCED DEVICE

(75) Inventors: Takeshi Mori, Machida (JP); Takemitsu Honda, Hino (JP); Masatoshi Homan, Hino (JP)

(73) Assignee: Olympus Corporation, Tokyo (JP)

( * ) Notice: Subject to any disclaimer, the term of this patent is extended or adjusted under 35 U.S.C. 154(b) by 1109 days.

(21) Appl. No.: 11/137,009

(22) Filed: May 24, 2005

(65) Prior Publication Data
US 2005/0261552 A1  Nov. 24, 2005

(30) Foreign Application Priority Data
May 24, 2004  (JP) .............................. 2004-153895

(51) Int. Cl.
*A61B 1/04* (2006.01)

(52) U.S. Cl. .................. 600/118; 600/101; 600/109

(58) Field of Classification Search ................ 600/101, 600/109, 117, 118, 160, 178, 407, 424, 476; 607/11, 27, 29
See application file for complete search history.

(56) References Cited

U.S. PATENT DOCUMENTS

| | | | | |
|---|---|---|---|---|
| 5,031,616 A * | 7/1991 | Mann et al. | ................... | 607/11 |
| 5,127,402 A * | 7/1992 | Mann et al. | ................... | 607/11 |
| 5,278,656 A * | 1/1994 | Hynecek et al. | ........ | 348/207.99 |
| 5,370,668 A * | 12/1994 | Shelton et al. | ................ | 607/29 |
| 5,402,769 A * | 4/1995 | Tsuji | .......................... | 600/109 |
| 6,166,518 A * | 12/2000 | Echarri et al. | ............... | 320/106 |
| 6,428,469 B1 | 8/2002 | Iddan et al. | | |
| 6,453,198 B1 * | 9/2002 | Torgerson et al. | ............ | 607/29 |
| 6,494,827 B1 * | 12/2002 | Matsumoto et al. | ......... | 600/118 |
| 6,584,355 B2 * | 6/2003 | Stessman | ..................... | 607/29 |
| 6,638,212 B1 * | 10/2003 | Oshima | ...................... | 600/109 |
| 6,748,273 B1 * | 6/2004 | Obel et al. | ..................... | 607/29 |
| 6,760,625 B1 * | 7/2004 | Kroll | ........................... | 607/29 |
| 6,804,557 B1 * | 10/2004 | Kroll | ........................... | 607/29 |
| 6,901,293 B2 * | 5/2005 | Rogers et al. | ................. | 607/29 |
| 6,940,255 B2 * | 9/2005 | Loch | .......................... | 320/132 |
| 7,194,308 B2 * | 3/2007 | Krig et al. | ..................... | 607/29 |
| 7,239,146 B2 * | 7/2007 | James et al. | ................ | 324/426 |
| 7,515,962 B2 * | 4/2009 | Lyden | ......................... | 607/29 |
| 2002/0158976 A1 * | 10/2002 | Vni et al. | .................... | 348/243 |
| 2003/0004397 A1 * | 1/2003 | Kameya et al. | ............. | 600/101 |
| 2005/0102005 A1 * | 5/2005 | Krig et al. | ..................... | 607/29 |

FOREIGN PATENT DOCUMENTS

JP  10262919 A  * 10/1998
WO  WO 01/35813 A1  5/2001

* cited by examiner

*Primary Examiner*—John P Leubecker
*Assistant Examiner*—Samuel Candler
(74) *Attorney, Agent, or Firm*—Scully, Scott, Murphy & Presser, P.C.

(57) ABSTRACT

An intrabody introduced device comprising: a power storage section for supplying driving power to a function executing section; a detecting section for detecting a supply voltage of the power storage section; and a timing output section for outputting a detection signal for use in detecting the supply voltage using the detecting section at given timing. The detection timing of the supply voltage can be controlled in this manner, and therefore the supply voltage can be detected at timing at which the load of function executing section is low, thereby enabling efficient voltage detection. For example, if the aforementioned timing is synchronized with the blanking period of a picked-up image, a stable voltage measurement is enabled at timing at which the intrabody introduced device applies a low load.

1 Claim, 6 Drawing Sheets

INTRABODY INTRODUCED DEVICE

CROSS-REFERENCE TO RELATED APPLICATION

This application is based upon and claims the benefit of priority from prior Japanese Patent Application No. 2004-153895, filed May 24, 2004, the entire contents of which is incorporated herein by reference.

BACKGROUND OF THE INVENTION

1. Field of the Invention

The present invention relates to an intrabody introduced device, and more particularly to detecting a supply voltage of a battery for the intrabody introduced device.

2. Description of the Related Art

In recent years, a capsule type endoscope has emerged as one of the intrabody introduced devices in the endoscope area. The capsule type endoscope has an imaging function and a wireless function. The capsule type endoscope is swallowed by a test subject as a test body for observation (examination) and then moves inside the stomach, the small intestine, or other organs (in the body cavity) with the organs' peristaltic motion for the observation period until it is excreted naturally from the test subject. The capsule type endoscope takes images of the inside of the organs sequentially by using the imaging function while it moves inside the organs.

Image data captured in the body cavity by the capsule type endoscope during the observation of the organs while moving inside thereof is transmitted to an external device provided outside the test body by using a wireless function (radio communication or the like) and then stored in a memory provided inside the external device. The test subject carries the external device, whereby the test subject is not restrained in behavior during the observation period until the capsule type endoscope is excreted after the test subject swallows the capsule type endoscope. After the observation, images of the inside of the body cavity are displayed on a screen of a display or the like on the basis of the image data stored in the memory of the external device, whereby a doctor or a nurse can make a diagnosis.

In this type of capsule type endoscope, there is a swallowable capsule type endoscope such as, for example, one disclosed in the brochure of International Publication No. 01/35813. This brochure suggests a capsule type endoscope provided inside with a reed switch turned on or off according to an external magnetic field and an arrangement in which the capsule type endoscope is contained in a package including a permanent magnet for supplying the external magnetic field in order to control driving of the capsule type endoscope. More specifically, the reed switch in the capsule type endoscope maintains the OFF state in an environment with a magnetic field of a certain or higher intensity, while it is turned on by a decrease in the intensity of the external magnetic field. Therefore, the capsule type endoscope is not driven in a condition where it is contained in the package. When the capsule type endoscope is taken out of the package for swallowing, the capsule type endoscope is separated from the permanent magnet and is not influenced any more by the magnetic force and thus starts to be driven. With this arrangement, it is possible to prevent the capsule type endoscope from being driven in the condition where it is contained in the package. After the capsule type endoscope is taken out of the package, it is driven and therefore takes images using the lighting function and the imaging function and transmits image signals using the wireless function.

The capsule type endoscope drives a function executing section for executing predetermined given functions such as a lighting function, an imaging function, and a wireless function by supplying power from a battery such as, for example, a button dry cell. Therefore, if the battery is used for a long period of time, the supply voltage of the battery decreases to a medium potential and the medium potential may cause latch-up or some other phenomenon in the load side of the function executing section, whereby the capsule type endoscope may enter a failure mode. To prevent such a phenomenon, the circuit can be configured so that the battery is disconnected from the function executing section in the medium potential. Current, however, is consumed also in a circuit for detecting the supply voltage of the battery. The prior art does not disclose or suggest reducing the power consumption of the circuit for detecting the supply voltage of the battery to increase the battery life.

This invention has made in view of the above problems, and has its object in providing an intrabody introduced device capable of reducing consumption of electric current used for detecting the current voltage of an electric source like a dry cell.

BRIEF SUMMARY OF THE INVENTION

According to an aspect of the present invention, there is provided an intrabody introduced device comprising: a power storage section for supplying driving power to a function executing section; a detecting section for detecting a supply voltage of the power storage section; and a timing output section for outputting a detection signal (for example, a pulse signal) for use in detecting the supply voltage using the detecting section at given timing. The detection timing of the supply voltage can be controlled in this manner, and therefore the supply voltage can be detected at timing at which the function executing section applies a low load, thereby enabling efficient voltage detection.

The intrabody introduced device may further comprise a power supply control section for at least reducing the power supply from the power storage section to the function executing section on the basis of a result of the detection obtained by the detecting section. With this arrangement, for example, if the voltage is equal to or smaller than a given value, it is possible to prevent an occurrence of a malfunction by stopping the power supply to the function executing section.

For example, the timing output section may output a detection pulse having a given length and the detecting section may detect the supply voltage during an output period of the detection pulse. In this condition, the generation of the pulse signal determines the timing of detecting the supply voltage, thereby achieving a simple circuit.

In the above, the timing output section can output the detection pulse at given timing synchronized with driving timing of the function executing section. Thereby, the supply voltage can be detected at the timing depending on a load of the device, thus enabling stable voltage detection.

The function executing section includes, for example, a lighting section for illuminating the inside of a test body, an acquisition section for acquiring image information inside the illuminated test body, and a radio transmission section for wirelessly transmitting the image information from the inside of the test body acquired by the acquisition section to outside the test body. In this condition, it is possible to output the detection pulse in synchronization with the driving timing of the acquisition section and during a period (blanking period)

other than the period of outputting the image information using the acquisition section. With this arrangement, the supply voltage can be detected during the blanking period. Due to a low load of the system during the blanking period, the supply voltage can be stably detected.

The intrabody introduced device according to the present invention outputs a signal for detecting the supply voltage using the detecting section from the timing output section. For example, it outputs the detection pulse only for a given length of a time period necessary for checking a consumption of the power storage section (e.g., battery) and detects the supply voltage during the time period.

BRIEF DESCRIPTION OF THE SEVERAL VIEWS OF THE DRAWINGS

These and other features, aspects, and advantages of the apparatus and methods of the present invention will become better understood with regard to the following description, appended claims, and accompanying drawings where:

DETAILED DESCRIPTION OF THE INVENTION

Preferred embodiments of the invention will be described below with reference to the accompanying drawings.

The present invention is not limited to these embodiments, but various changes may be made without departing from the scope of the invention.

Figure 1:
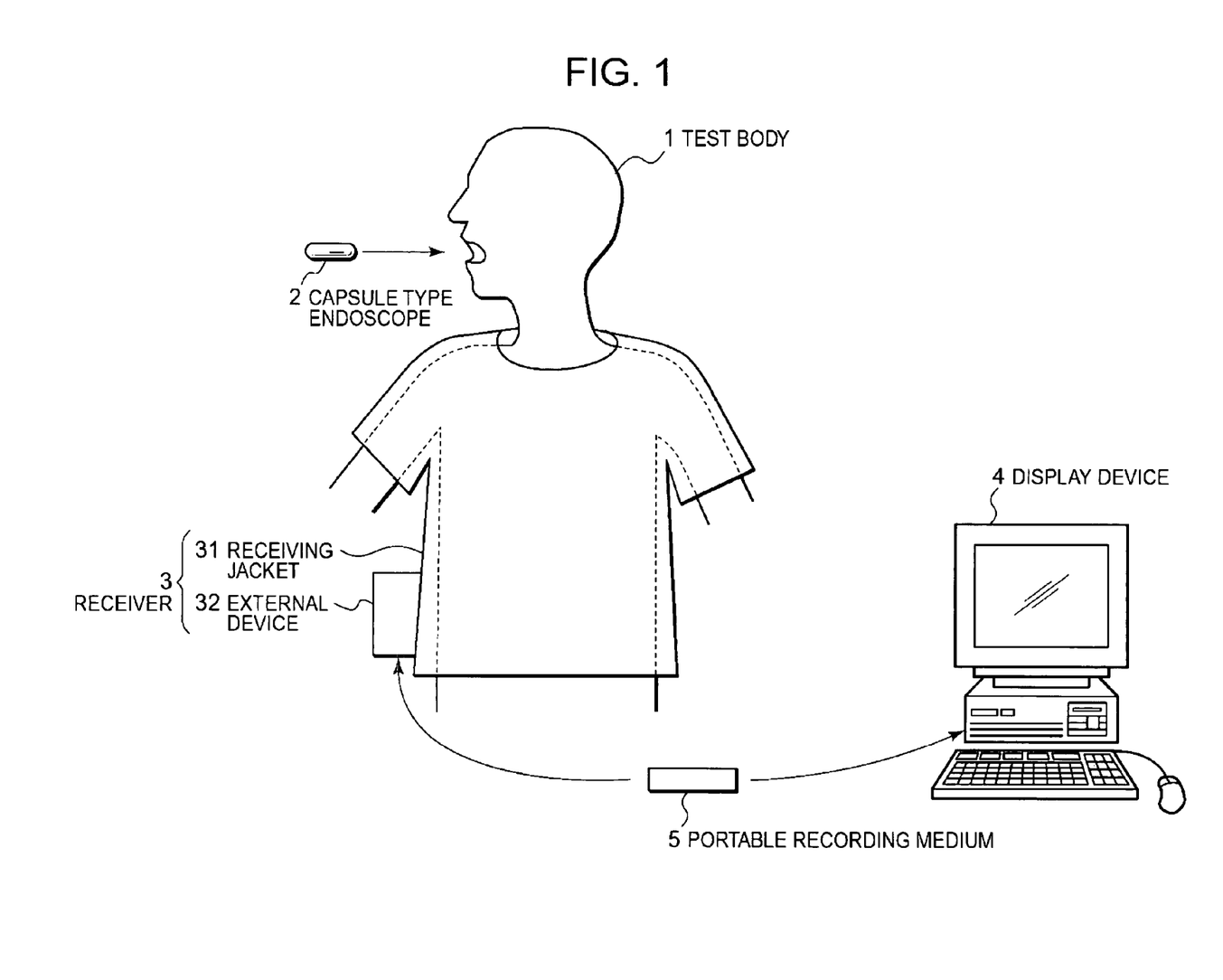
FIG. 1 is a schematic diagram showing a general configuration of a wireless intrabody information acquisition system including an intrabody introduced device according to a first embodiment.

Referring to FIG. 1, there is shown a schematic diagram of a general configuration of a wireless intrabody information acquisition system including an intrabody introduced device according to a first embodiment. This wireless intrabody information acquisition system will now be described below by giving an example of a capsule type endoscope as the intrabody introduced device. Those skilled in the art will appreciate that the capsule type endoscope is used by way of example only and that other intrabody introduced devices can also be used without departing from the spirit and scope of the claimed invention. In FIG. 1, the wireless intrabody information acquisition system comprises a receiver 3 having a wireless receiving function and a capsule type endoscope (intrabody introduced device) 2, which is introduced into a test body 1 to pick up images of the inside of the body cavity and transmits data such as image signals to the receiver 3. The wireless intrabody information acquisition system further comprises a display device 4 for displaying the images of the inside of the body cavity on the basis of the image signals received by the receiver 3 and a portable recording medium 5 for passing data between the receiver 3 and the display device 4. The receiver 3 includes a receiving jacket 31 worn by the test body 1 and an external device 32 for processing radio signals received. The capsule type endoscope 2 and the receiver 3 constitute a medical device according to the present invention.

The display device 4 is for use in displaying the images of the inside of the body cavity picked up by the capsule type endoscope 2. The display device 4 may be a work station for displaying images on the basis of data acquired by the portable recording medium 5, for example. Specifically, the display device 4 may be configured to display images directly by means of a CRT display or a liquid crystal display. Furthermore, the display device 4 may be configured to output images to another medium other than a display, such as a printer.

The portable recording medium 5 is removable from the external device 32 and the display device 4. When the portable recording medium 5 is inserted into such devices, it can output or record information. In this embodiment, the portable recording medium 5 is inserted into the external device 32 and records data transmitted from the capsule type endoscope 2 while the capsule type endoscope 2 moves inside the body cavity of the test body 1. After the capsule type endoscope 2 is excreted from the test body 1, in other words, after completion of imaging of the inside of the test body 1, the portable recording medium 5 is then removed from the external device 32 and inserted into the display device 4 and the display device 4 reads out the data recorded by the portable recording medium 5. The data is passed between the external device 32 and the display device 4 by means of the portable recording medium 5 in this manner, thereby permitting the test body 1 to move more freely during imaging of the inside of the body cavity than in a case where the external device 32 is directly connected to the display device 4 via a fixed line. For example, the aforementioned portable recording medium 5 can be a CompactFlash® (CF) memory. Note that, however, the portable recording medium 5 has been used for passing data between the external device 32 and the display device 4 here, but it is not necessarily limited to this. For example, another internal recording device (a hard disk or the like) may be used instead of the external device 32 and be connected to the display device 4 via a fixed line or wirelessly for passing data to the display device 4.

Figure 2:
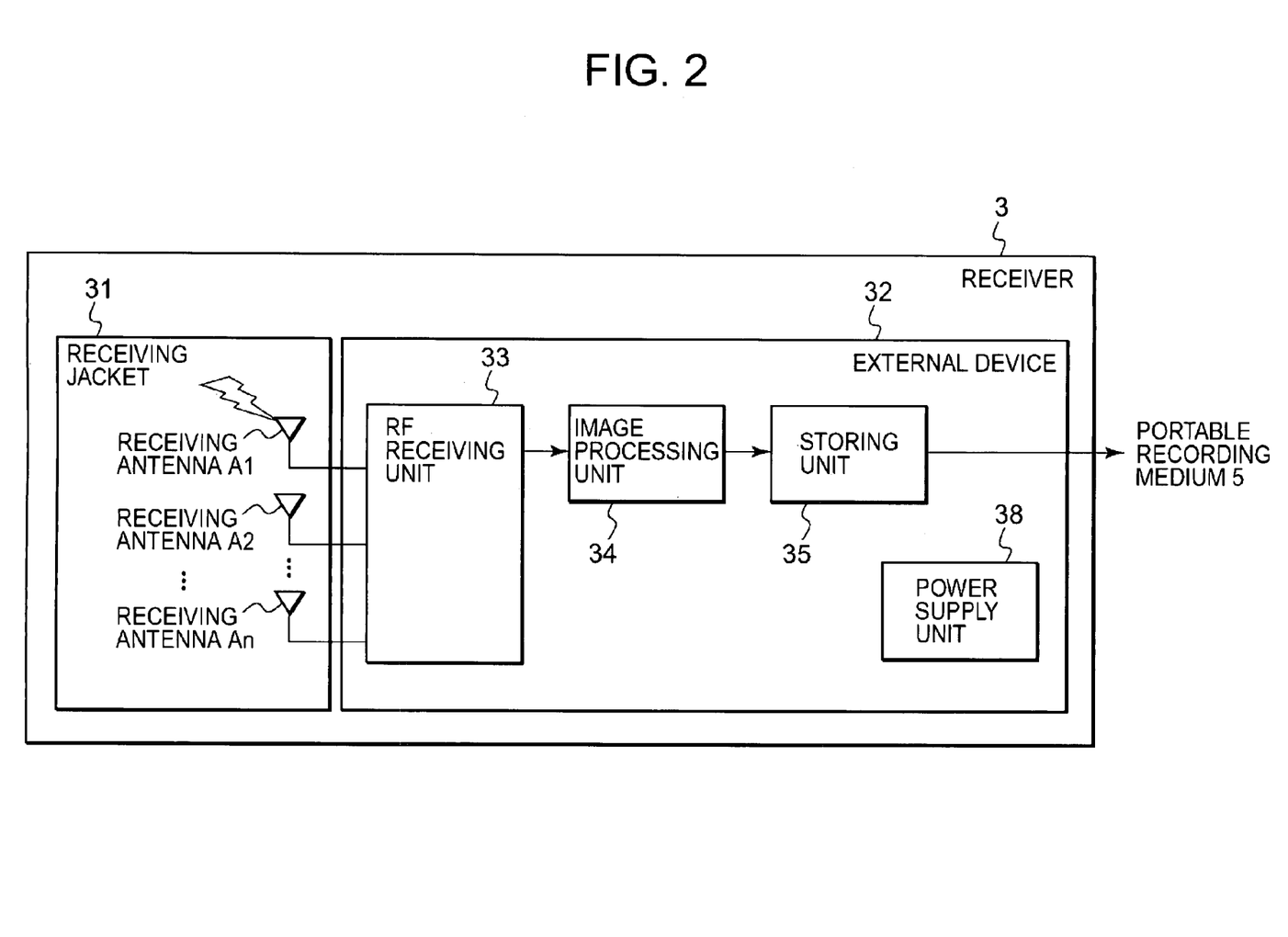
FIG. 2 is a block diagram showing a configuration of the receiver shown in FIG. 1.

Subsequently, the configuration of the receiver 3 will be described with reference to the block diagram shown in FIG. 2. The receiver 3 has a function of receiving image information on the inside of the body cavity wirelessly transmitted from the capsule type endoscope 2. As shown in FIG. 2, the receiver 3 is provided with the receiving jacket 31 and the external device 32. The receiving jacket 31 has a form enabling the test body 1 to wear it, having receiving antennas A1 to An. The external device 32 processes radio signals received via the receiving jacket 31. The receiving antennas A1 to An can be directly adhered to an outer surface of the test body, instead of being provided in the receiving jacket 31. The receiving antennas A1 to An can also be detachable from the receiving jacket 31.

The external device 32 includes an RF receiving unit 33, an image processing unit 34, a storing unit 35, and a power supply unit 38. The RF receiving unit 33 performs given signal processing such as demodulation for radio signals received by the receiving antennas A1 to An and extracts image information acquired by the capsule type endoscope 2 out of the radio signals. The image processing unit 34 performs image processing necessary for the image information extracted by the RF receiving unit 33. The storing unit 35 records the image information image-processed by the image processing unit 34. In this manner, the external device 32 performs signal processing of the radio signals transmitted from the capsule type endoscope 2. In this embodiment, the image information is recorded into the portable recording medium 5 via the storing unit 35. Furthermore, the power supply unit 38 has a given capacitor or AC adapter. The components of the external device 32 use power as driving energy supplied from the power supply unit 38.

Subsequently, the configuration of the capsule type endoscope 2 will be described by using the block diagram shown in FIG. 3. As shown in the block diagram in FIG. 3, the capsule type endoscope 2 includes a light emitting device (LED) 20, an LED driving circuit 21, a charge coupled device (CCD) 23, a CCD driving circuit 24, a signal processing circuit 25, an image pickup timing generation circuit 26. The light emitting device (LED) 20 is a lighting section for irradiating an examined area in the body cavity of the test body 1. The LED driving circuit 21 controls a driven state of the LED 20. The charge coupled device (CCD) 23 is an acquisition section that captures images of the inside of the body cavity (information on the inside of the test body) formed by a reflected light from the area irradiated by the LED 20. The CCD driving circuit 24 controls a driven state of the CCD 23. The signal processing circuit 25 processes image signals output from the CCD 23 to acquire image information in a desired format. The image pickup timing generation circuit 26 is a timing output section for outputting reference clock pulses for use in giving driving timing such as the timing of turning on the LED 20 or the image pickup timing of the CCD 23, together with the signal processing circuit 25. The capsule type endoscope 2 further includes an RF transmission unit 27 for modulating the picked-up image information to RF signals and a transmission antenna 28 as a radio transmission section for wirelessly transmitting the RF signals output from the RF transmission unit 27. The capsule type endoscope 2 further includes a system control circuit 29 for controlling operations of the LED driving circuit 21, the CCD driving circuit 24, and the RF transmission unit 27 and a battery 30 as a power storage section for supplying power to these electrical apparatuses. The CCD 23, the CCD driving circuit 24, the signal processing circuit 25, and the image pickup timing generation circuit 26 are included in the imaging section 22. With the provision of these mechanisms, the capsule type endoscope 2 acquires the image signals of the examined area, irradiated by the LED 20, by the CCD 23 while it is introduced into the test body 1, on the basis of the reference clock pulses representing desired image pickup timing. The acquired analog image signals are submitted to signal processing by the signal processing circuit 25 on the basis of the reference clock pulses, converted to RF signals by the RF transmission unit 27, and then transmitted to the outside of the test body 1 via the transmission antenna 28.

Figure 3:
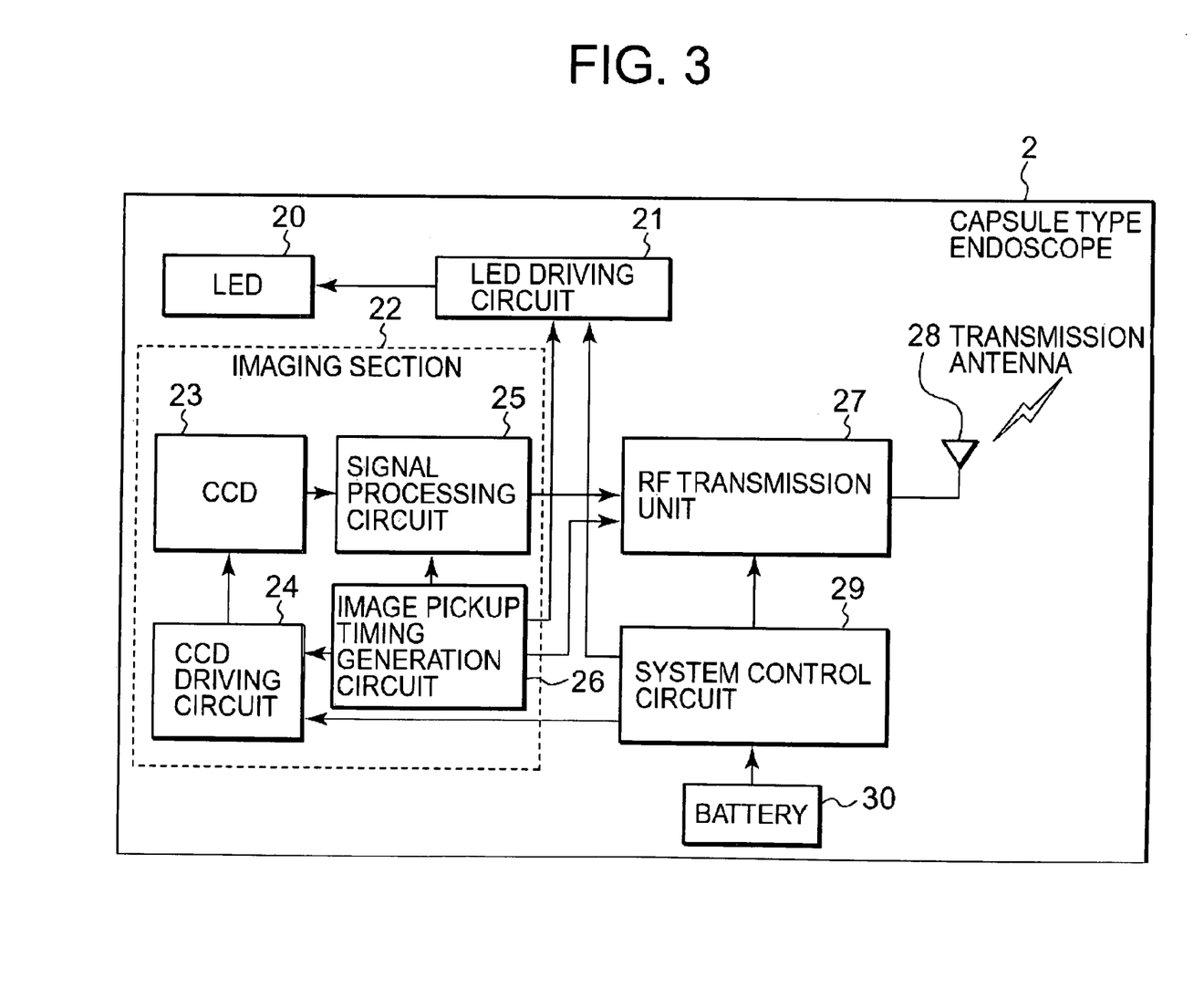
FIG. 3 is a block diagram showing a configuration of the capsule type endoscope shown in FIG. 1.
Figure 4:
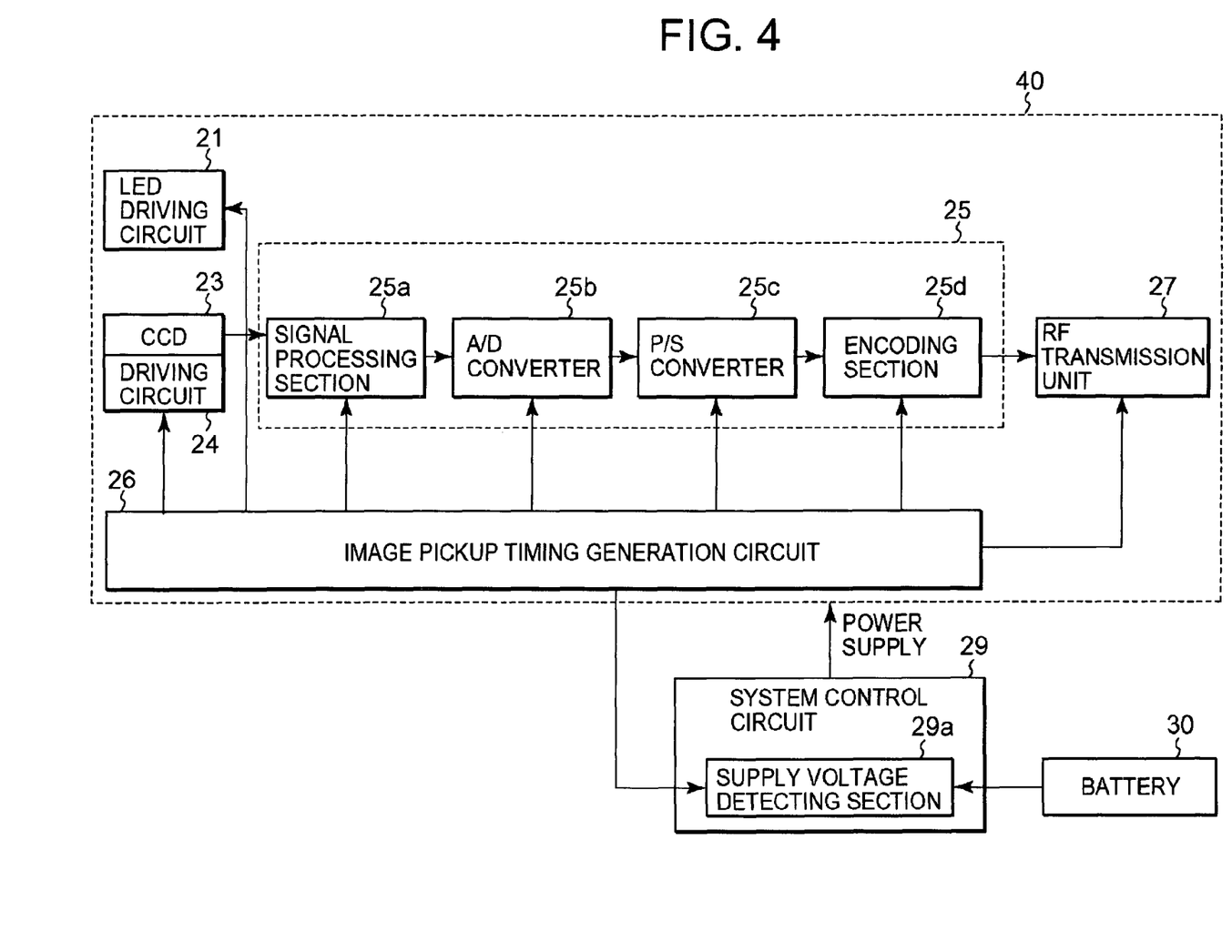
FIG. 4 is a block diagram showing the first embodiment of a configuration of the image pickup timing shown in FIG. 3.

Referring to FIG. 4, there is shown a block diagram of a configuration of the image pickup timing system shown in FIG. 3. In FIG. 4, the image pickup timing generation circuit 26 outputs the reference clock pulses, as a basis of driving timing, to the LED driving circuit 21, the CCD driving circuit 24, the signal processing circuit 25, and the RF transmission unit 27. The signal processing circuit 25 includes a signal processing section 25*a*, an A/D converter 25*b*, a P/S converter 25*c*, and an encoding section 25*d*. The signal processing section 25*a* performs desired signal processing for the image signals output from the CCD 23. The A/D converter 25*b* converts the analog image signals to digital image information. The P/S converter 25*c* performs a parallel-to-serial conversion of image information. The encoding section 25*d* encodes image information.

Figure 5:
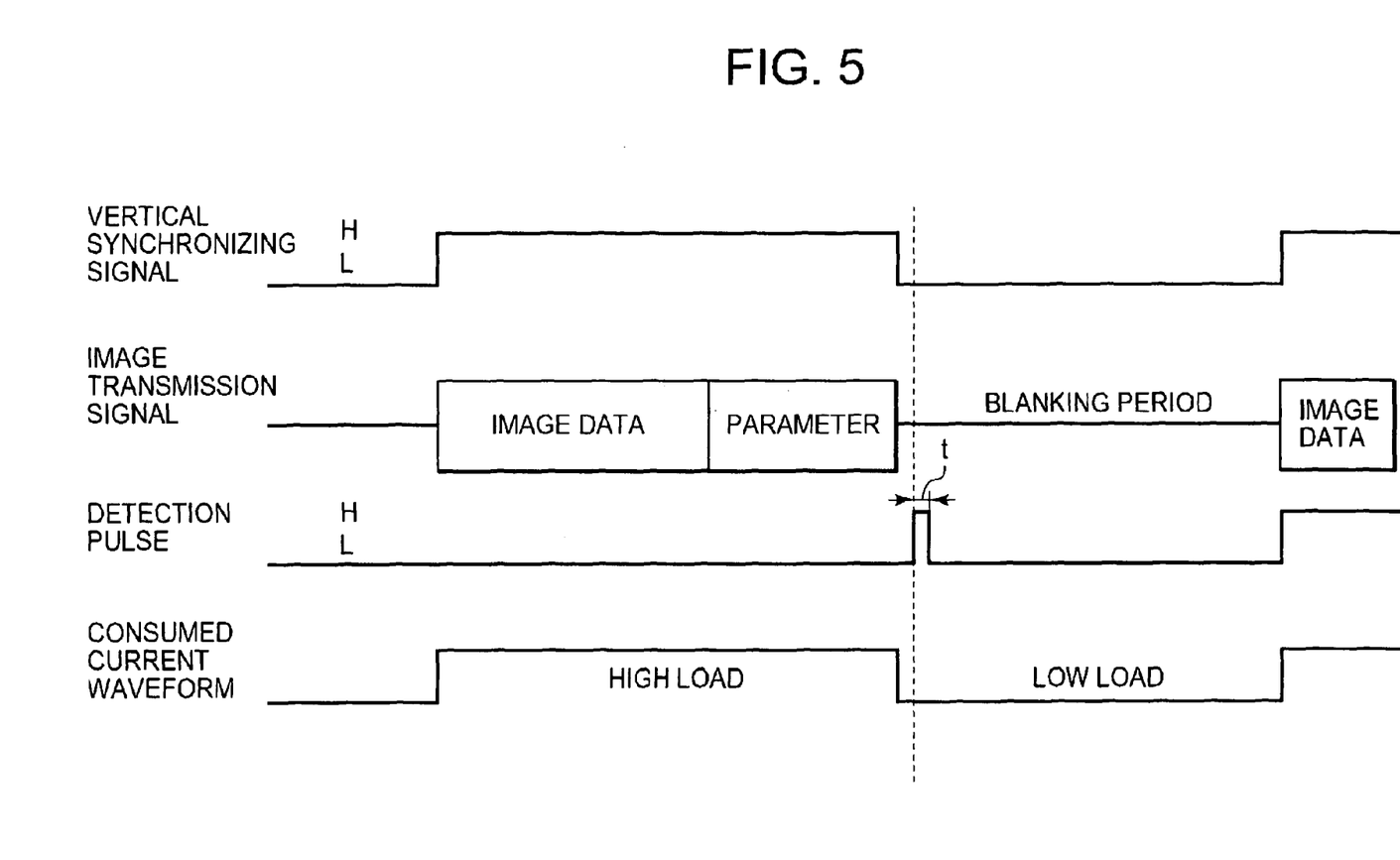
FIG. 5 is a waveform diagram showing output timings of various parts of the image pickup timing system shown in FIG. 4.

The image pickup timing generation circuit 26 has a function of a timing output section and outputs a detection pulse for detecting a voltage of the battery to a supply voltage detecting section 29*a* in a system control circuit 29 as shown in the waveform diagram of FIG. 5. The detection pulse is synchronized with, for example, the timing of driving the CCD driving circuit 24 and output to the supply voltage detecting section 29*a* at given timing during the blanking period other than the output period of the image information using the CCD driving circuit 24. In FIG. 5, the output period of the image transmission signal (image information) is synchronized with the high (H) state period of a vertical synchronizing signal. During the blanking period, other parts of the function executing section are not driven and therefore the load is low and consumed current is relatively stable. This ensures pulse detection in the supply voltage detecting section 29*a* and prevents a malfunction. The detection pulse is output only for a given length of time period t necessary for checking the consumption of the battery 30. This facilitates detection of the detection pulse in the supply voltage detecting section 29*a*. The detection pulse can be output at any timing only if it is during the blanking period.

The system control circuit 29 has a function of distributing the driving power supplied from the battery 30 to other components (function executing section). In this embodiment, components having the imaging function, the lighting function, and the wireless function (partial) of the capsule type endoscope 2 are generically called a function executing section for executing the given functions. Specifically, the components other than the system control circuit 29 correspond to the function executing section for executing the given functions and they are generically called an intra-capsule function executing circuit 40 hereinafter, if necessary.

Figure 6:
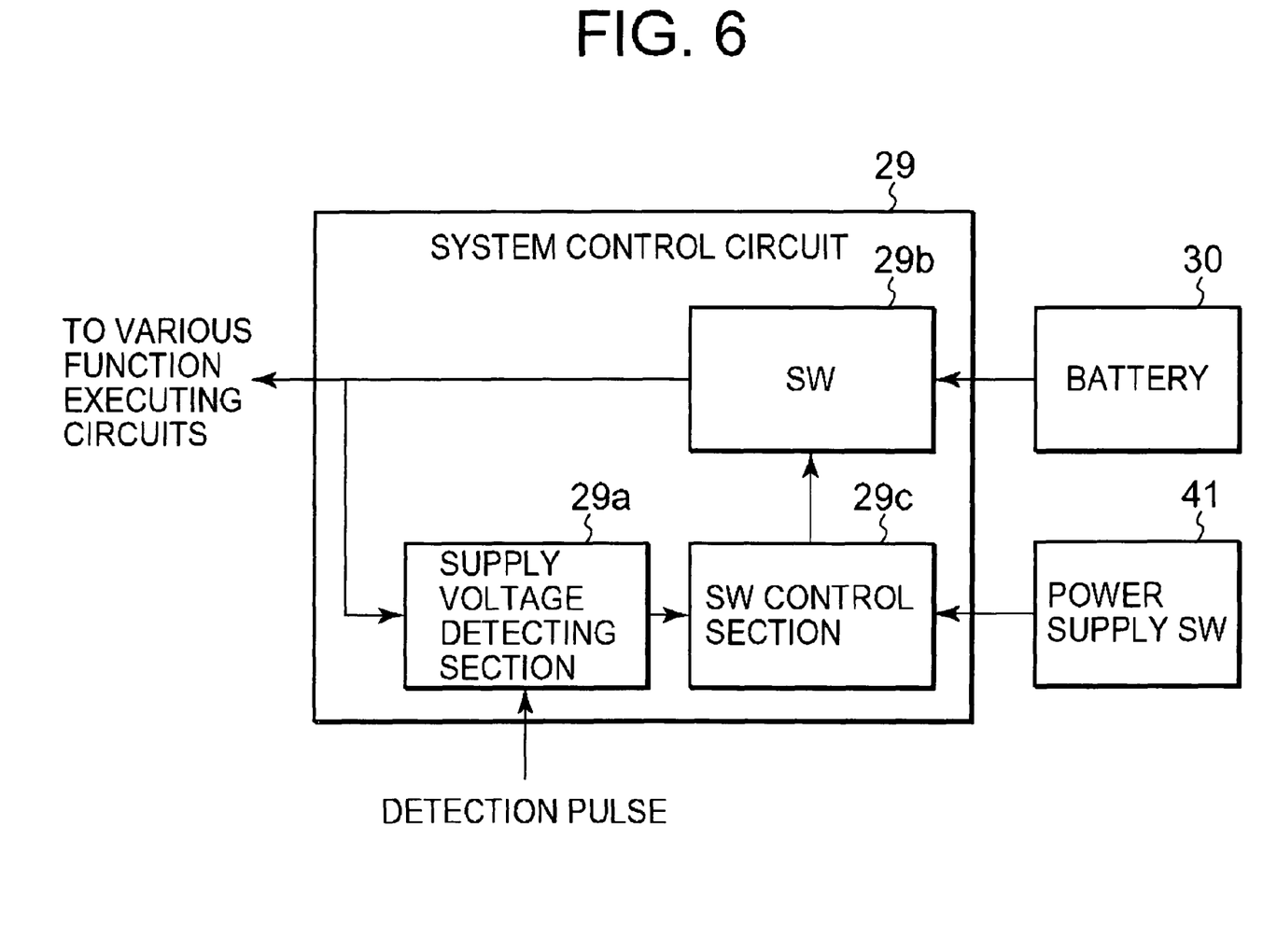
FIG. 6 is a block diagram showing a configuration of the system control circuit shown in FIG. 4.

As shown in FIG. 6, the system control circuit 29 includes a switch 29*b* and a switch control section 29*c* besides the supply voltage detecting section 29*a* as the detecting section for detecting the supply voltage of the battery 30. The switch 29*b* is disposed between the supply voltage detecting section 29*a* and the battery 30 and enables the battery 30 to supply power to the intra-capsule function executing circuit 40. The switch control section 29*c* is a power supply control section for controlling a selection of the switch 29*b* on the basis of a result of detecting a voltage of the supply voltage detecting section 29*a*. The supply voltage detecting section 29*a* detects a supply voltage of the battery 30 during the given length of time period (a pulse width in the high state) t of the detection pulse output from the image pickup timing generation circuit 26 and outputs the result of the detection to the switch control section 29*c*. The switch control section 29*c* is connected to a power supply switch 41 composed of a reed switch, which is turned on or off according to an externally applied magnetic field. The power supply switch 41 is configured to maintain the ON state once a magnetic field is applied, for example. Upon an input of a result of detecting a supply voltage from the supply voltage detecting section 29*a*, the switch control section 29*c* makes an ON-OFF control of the switch 29*b* on the basis of the result of the detection.

Specifically, if the power supply switch 41 is turned on by an external application of a magnetic field, the switch control section 29*c* selects the ON state of the switch 29*b* to enable the battery 30 to supply driving power to the intra-capsule function executing circuit 40. Subsequently, the image pickup timing generation circuit 26 outputs a detection pulse for detecting a voltage of the battery 30 during the blanking period of the image transmission signal to the system control circuit 29. Thereupon, the supply voltage detecting section 29*a* of the system control circuit 29 detects a supply voltage during the high state period of the detection pulse. The system control circuit 29 determines whether the voltage value is equal to or higher than a preset threshold (for example, a voltage value permitting the image information to be acquired in the test body during the examination period until a capsule type endoscope is excreted after the test subject swallows down the capsule type endoscope) and outputs the determination result to the switch control section 29c.

If the detected supply voltage value is equal to or higher than the preset threshold, for example, as the determination result, the switch control section 29c determines that the image information can be acquired during the examination period and maintains the ON state of the switch 29b. If the detected supply voltage value is lower than the threshold, for example, as the determination result, the switch control section 29c determines that it is hard to acquire the image information during the examination period at the current supply voltage of the battery 30 and thus selects the OFF state of the switch 29b to substantially stop the power supply from the battery 30 to the intra-capsule function executing circuit 40.

As stated hereinabove, in this embodiment, the detection pulse having the given length necessary for detecting the supply voltage of the battery is output from the image pickup timing generation circuit in synchronization with the CCD driving timing. Furthermore, the supply voltage detecting section detects a supply voltage during the detection pulse generation period and the switch control section controls the power supply to the intra-capsule function executing circuit on the basis of the detection result. This decreases the supply voltage detection period, thereby reducing battery current consumed by detecting the supply voltage.

Furthermore, in this embodiment, the detection pulse is output during the blanking period other than the image information output period (namely, the image transmission signal output period). Therefore, the intra-capsule function executing circuit is not driven, which leads to a low load on the power supply of the battery and to relatively stable consumed power. This ensures the pulse detection in the supply voltage detecting section. The detection pulse output period is not limited to the blanking period, but can be any period where the load is low and the consumed current is stable during the period.

Still further, in this embodiment, the point of detecting a supply voltage using the supply voltage detecting section is disposed on the output side of the switch of the system control circuit, thereby preventing a leak current that occurs when it is disposed on the input side of the switch and reducing battery current consumed by detecting the supply voltage.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be construed to cover all modifications that may fall within the scope of the appended claims.

What is claimed is:

1. A method of controlling a power supply from an internal battery of a capsule type endoscope, comprising:
    generating a pulse signal exclusively during a blanking period of an image signal captured by the capsule type endoscope;
    detecting a voltage of the internal battery of the capsule type endoscope during an output period of the pulse signal; and
    at least reducing the power supply from the internal battery if the voltage is lower than a given voltage.

* * * * *